United States Patent [19]

Junusov et al.

[11] Patent Number: 4,656,178
[45] Date of Patent: Apr. 7, 1987

[54] PHARMACEUTICAL COMPOSITION POSSESSING ANTIARRHYTHMIC EFFECT

[76] Inventors: Sabir J. Junusov, ulitsa Timiryazeva, 18; Marat S. Junusov, ulitsa Muminova, 7, kv. 19; Vladimir A. Telnov, ulitsa Muminova, ½, kv. 52; Farkhad N. Dzhagangirov, mikroraiom Akhmed-Danish, 3a, kv. 11, all of Tashkent; Fakhritdin Satritdinov, Kalininsky raion kolkhoz imeni M.I. Kalinina, Tashkentskaya oblast; Karimzhan Taizhanov, ulitsa Muminova, 10, kv. 58, Tashkent, all of U.S.S.R.

[21] Appl. No.: 726,283

[22] Filed: Apr. 24, 1985

Related U.S. Application Data

[63] Continuation of Ser. No. 528,600, Sep. 1, 1983, abandoned.

[51] Int. Cl.$^4$ ............................................. A61K 31/44
[52] U.S. Cl. .................................... 514/279; 514/821
[58] Field of Search ........................................ 514/279

[56] References Cited

PUBLICATIONS

*Chemical Abstracts*, vol. 92 (1980) 124912t; vol. 78 (1973) 92484x; vol. 89 (1978) 140208m.

*Primary Examiner*—Frederick E. Waddell
*Attorney, Agent, or Firm*—Burgess, Ryan & Wayne

[57] ABSTRACT

A novel pharmaceutical composition possessing an antiarrhythmic effect comprises an active principle - a hydrobromide salt of an alkaloid, viz. lappaconitine having the following formula

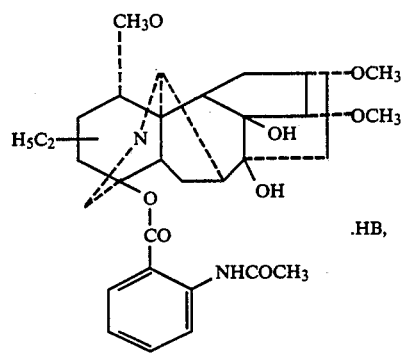

The composition of the present invention is used in the treatment of various diseases accompanied by the heart rhythm disturbances such as is chemic heart disease, diverse kinds of cardiomyopathy and the like.

4 Claims, No Drawings

PHARMACEUTICAL COMPOSITION POSSESSING ANTIARRHYTHMIC EFFECT

This application is a continuation, of application Ser. No. 528,600, filed Sept. 1, 1983, now abandoned.

TECHNICAL FIELD

The present invention relates to the art of medicine and, more specifically, it relates to a novel pharmaceutical composition useful in the treatment of various diseases accompanied by the heart rhythm disturbances such as ischemic heart disease, diverse kinds of cardiomyopathy and the like.

BACKGROUND OF THE INVENTION

Known in the art are various antiarrhythmic-action preparations such as quinidine, novocainamide ($\beta$-diethylaminoethylamide hydrochloride of p-aminobenzoic acid), obzidan (propranolol), isoptin, moricizin, ethmozin and others.

These preparations are widely used in the medical practice. However, they feature a number of disadvantages, namely an insufficient activity, a pronounced hypotensive effect, a short duration of the effect ensured by the preparation.

It is an object of the present invention to provide a novel pharmaceutical composition which possesses a higher antiarrhythmic activity, a longer duration and a broader range of the pharmacological action without reducing the arterial pressure.

This object is accomplished by the pharmaceutical composition possessing antiarrhythmic effect according to the present invention which is novel and hitherto unknown from the literature.

BRIEF DESCRIPTION OF THE INVENTION

The pharmaceutical composition possessing antiarrhythmic effect according to the present invention comprises an active principle and a pharmaceutically acceptable vehicle; as the active principle it contains a hydrogen bromide salt of an alkaloid, viz. lappaconitine of the following formula:

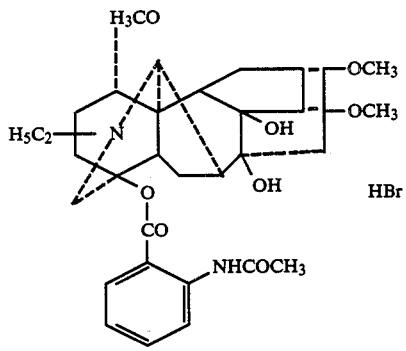

The pharmaceutical composition according to the present invention is preferably administered as injections or per os in the form of tablets.

The tabletted pharmaceutical composition according to the present invention preferably contains the active principle in the amount of 0.05 g per tablet. As the pharmaceutically acceptable vehicle for tablets it preferably contains saccharose and starch.

The pharmaceutical composition according to the present invention in the form of injections preferably contains 0.5% by weight of the active principle and, as the pharmaceutically acceptable vehicle, a solvent—distilled water. As regards its antiarrhythmic activity, the pharmaceutical composition according to the present invention is superior to the known antiarrhythmic agents currently employed such as quinidine and novocainamide.

A distinctive feature of the preparation according to the present invention resides in a long duration of its effect which is 10 times as long as that of quinidine and novocainamide.

The antiarrhythmic effect of the pharmaceutical composition according to the present invention is not accompanied by reduction of the systemic arterial pressure, and a negative inotropic effect on the cardiac tissue. These properties of the preparation according to the present invention are effectively combined with the presence of moderate coronarydilating, spasmolytic, local anesthetic, anti-inflammatory and sedative effects.

DETAILED DESCRIPTION OF THE INVENTION

The pharmaceutical composition according to the present invention can be administered in the following cases: treatment of substantially all kinds of rhythm disturbances of both ventricular and supraventricular origin caused by an enhanced ectopic excitability; diverse ventricular extrasystoles in myocardial infarction; lasting peroral treatment in the case of ventricular and supraventricular extrasystoles and preventive antirecurrent treatment in the case of paroxysmal tachycardiae and prophylaxis of cardiac rhythm disturbances; in operations on heart and major vessels; after an electropulsation treatment; at auricular fibrillation and flutter in combination with ventricular tachycardia; in the case of sinus tachycardia and rhythm disturbances at neurosis with hypersylmaticotonia, psychic and physical stresses, hyperthyroidism; cardiac rhythm disturbances at a cardiogenic shock; as a preventive measure against heart fibrillation in myocardial infarction.

The preparation according to the present invention has been experimentally tested on animals and on human beings under clinical conditions.

The assessment of the antiarrhythmic activity of the preparation was effected in acute and chronical experiments on rats, rabbits, cats and dogs. Various experimental models of arrhythmia were also used.

The atrioventricular arrhythmia caused by aconitine is one of the most reliable models for forecasting the efficiency of the antiarrhythmic action of the novel preparation in clinics. The experiments were conducted on both narcotized and non-narcotized animals. The preparation was administered per os, intramuscularly, intraperitoneally and intravenously 5 to 15 minutes prior to or 3–5 minutes after the administration of aconitine.

The duration of the antiarrhythmic action of the preparation was studied on rats intravenously administered with aconitine 1, 2, 4, 6, 24 and 48 hours after the preparation administration per os.

It has been found that the antiarrhythmic effect of the preparation according to the present invention is revealed beginning with the dose of 0.03 mg/kg. In doses of 0.2–0.5 mg/kg the preparation of this invention prevents the appearance of aconitine arrhythmia in 100% of the rats. A repeated administration of the same dose of aconitine to the same animals 5–10 days thereafter without any preliminary administration of the preparation according to the present invention has resulted in appearance of arrhythmia in 100% of the rats. Under similar experimental conditions a preliminary administration of novocainamide in the dose of 60 mg/kg intravenously produced an antiarrhythmic effect in 50% of the animals.

In a similar case, upon administration of quinidine the antiarrhythmic effect in 50% of the animals was observed at the dose of 20 mg/kg.

The data obtained in respect of the effect of novocainamide and quinidine on the aconitine arrhythmia coincide with the literature data. Lidocaine and trimecaine in doses of 5-10 mg/kg prevent origination of aconitine arrhythmia for 3-5 minutes, while in doses of 20 mg/kg and more they cause perdition of a portion of the narcotized rats prior to administration of aconitine. The preventive administration of obzidan to the rats in the dose of 5 mg/kg retarded the time of appearance of aconitine arrhythmia for 5-8 minutes in all test rats, whereafter in 60% of the animals arrhythmia was developed.

Isoptin administered in doses of 0.1-2.5 mg/kg did not prevent the development of aconitine arrhythmia.

Therefore, the prophylactic effect of the pharmaceutical composition according to the present invention on the development of aconitine arrhythmia is considerably superior over all the compared antiarrhythmic preparations. Its antiarrhythmic index ($LD_{50}/ED_{50}$) is equal to 118.0 far exceeding quinidine and novocainamide with the antiarrhythmic index thereof equal to 2.75 and 2.3 respectively.

The antiarrhythmic activity of the pharmaceutical composition according to the present invention upon administration thereof against the background of a developing aconitine arrhythmia (therapeutic effect) was studied on 110 narcotized rats. The preparation was intravenously administered at intervals of 3-6 minutes against the background of the originated arrhythmia. It has been found that in the dose of 0.1 mg/kg the preparation according to the present invention results in a complete restoration of a normal sinus rhythm in 50% of the animals 30-35 minutes after its administration (in control experiments the aconitine errhythmia lasts for 120 minutes). The administration of the preparation according to the present invention in a dose of from 0.3 to 0.5 mg/kg after 1-2 minutes results in a complete elimination of arrhythmia and restoration of the correct sinus rhythm in all the animals. Under similar conditions novocainamide in the dose of 20 mg/kg restored a normal sinus rhythm in 3 rats out of 6 for 10 minutes on the average and then a stable arrhythmia appeared again. At the dose of 40 mg/kg the antiarrhythmic effect of novocainamide was noticed in 83.3% of the animals, but in 50% of the rats the effect was observed during the first 20 minutes and then a stable arrythmia reappeared. Quinidine in doses of 2.5, 5, 10, 20 mg/kg against the background of a developing aconitine arrhythmia revealed no antiarrhythmic activity. The administration of lidocaine (5-10 mg/kg) under similar conditions produced a short-time (0.5 to 3 minutes) arrhythmia-arresting effect, followed by the development of arrhythmia. The administration of thrimecaine, obzidan, and isoptin under similar conditions also turned out to be inefficient. The antiarrhythmic index of the preparation according to the present invention ($LD_{50}/ED_{50}$)=59 against the background of a developing aconitine arrhythmia was far above that of the next-to-it (in activity) novocainamide with its antiarrhythmic index of 6.9.

The study of the antiarrhythmic effect of the pharmaceutical composition according to the present invention on narcotized rats and dogs has shown that upon an intravenous administration in doses of 0.2-0.3 mg/kg it fully prevents the development of aconitine arrhythmia in 100% of the animals. In doses of 0.5 and 1 mg/kg the preparation of the present invention fully prevents a lethal fibrillation of the heart induced by aconitine in rats. In experiments on dogs and intact rats it has been shown that the peroral administration of the preparation in doses of 1-2 mg/kg fully prevents the development of the aconitine arrhythmia in 100% of the animals. Therefore, the pharmaceutical composition according to the present invention, as tested on the aconitine model of arrhythmia, is considerably superior, in its activity, duration (up to 24 hours) and range of antiarrhythmic action, over the prior art preparations such as quindine, novocainamide, lidocaine, trimecaine, isoptin and obzidan.

The study of the antiarrhythmic activity of the preparation according to the present invention on a model of cardiac arrhythmia induced by barium chloride was carried out on 56 narcotized rats and 16 intact rabbits. The preparation of the present invention in the dose of 0.1 mg/kg injected 10 minutes prior to administration of barium prevented the development of arrhythmia in 86.6% of the animals. Under similar experimental conditions quinidine in the dose of 10 mg/kg approximately corresponded to the antiarrhythmic effect produced by the preparation according to the present invention in the dose of 0.1 mg/kg. On a given model of cardiac arrhythmia the weakest antiarrhythmic activity was revealed by novocainamide which was in agreement with the literature data.

The effect of the preparation according to the present invention on the cardiac arrhythmia caused by ligation of the descending branch of the left coronary artery by the Harris method was studied in experiments on dogs. The preparation according to the present invention was intravenously administered on the first and second postoperative days. Preliminarily, prior to every experiment 30 to 45 minutes before the administration of the preparation the background changes of the dogs' electrocardiogram (ECG) were recorded. The antiarrhythmic effect of the preparation according to the present invention in the dose of 0.5 mg/kg was observed in 86% of the animals. In the dose of 1 mg/kg a full inhibition of the ventricular extrasystole was observed in 100% of the animals. In 40% thereof a full suppression of ectopic contractions was noticed for 3-3.5 hours, whereafter arrhythmia appeared with the intensity thereof not reaching the initial background during 7 hours.

In 60% of the animals the duration of a 100% antiarrhythmic effect was far more lasting—over 5 hours with a subsequent gradual restoration of arrhythmia. In all of the experiments the reduction or full arresting of arrhythmia was accompanied by reduction of the heart beat rate. The antiarrhythmic effect appeared 5-15 minutes after the administration and was in a direct relationship with the administered dose. Under similar experimental conditions novocainamide produced the antiarrhythmic effect in doses of 40-50 mg/kg and the effect occurred very rapidly, but lasted for only 4-7 minutes, whereafter ventricular extrasystole and tachycardia reappeared. In a dose of 70-80 mg/kg the effect lasted for 30-60 minutes.

Quinidine in a dose of 5–10 mg/kg produced a weak effect on the cardiac arrhythmia caused by ligation of the descending branch of the left coronary artery in dogs which corresponded to the literature data.

Therefore, on this model of cardiac arrhythmia the preparation according to the present invention proved to be by 70 times more active than novocainamide; it is considerably superior to it in the duration of the effect, but inferior to novocainamide in the rapidity of occurrence of the antiarrhythmic effect.

The preparation according to the present invention in the doses of 0.25 and 0.5 mg/kg (intravenously) fully stops the origination of arrhythmia caused by electrical irritation of auricular of the right auricle and apex of the left ventricle in all of the animals (7 dogs and 10 cats).

The antiarrhythmic effect of the preparation according to the present invention develops 3–7 minutes after administration and retains for 2–3 hours. The arterial pressure and amplitude of the heart beat are not changed. Under similar experimental conditions novocainamide and quinidine in the dose of 10 mg/kg produce, for 2–5 minutes, an antiarrhythmic effect in 40% and 30% of the animals respectively.

In a dose of 20–30 mg/kg the effect of both preparations lasted for 20–25 minutes. In all the tested doses novocainamide and quinidine caused reduction of the arterial pressure by 20–70 mm Hg and bradycardia. The antiarrhythmic effect of novocainamide occurred 1.0–1.5 minutes and that of quinidine-2–3 minutes after an intravenous administration. Consequently, on a given model of cardiac arrhythmia the pharmaceutical composition according to the present invention is by 40 times superior to quinidine and novocainamide in the activity thereof; its antiarrhythmic effect develops slowly but is retained for a much longer time and not accompanied by reduction of the arterial pressure in the animals.

The preparation according to the present invention in a dose of 0.1–0.2 mg/kg cuts short the arrhythmia induced by adrenalin in dogs preliminarily subjected to ligation of the descending branch of the left coronary artery.

The maximum effect is developed within 5–10 minutes and retains for more than 2 hours.

In the above-specified doses the preparation does not affect the level of arterial pressure or the height of elevation of arterial pressure (hypertension) caused by adrenalin.

With the view to evaluate the effect of the preparation according to the present invention on arterial pressure and breathing, experiments have been carried out on narcotized cats and dogs. It was found that the intravenous administration of the preparation according to the present invention in the doses of 0.05, 0.1, 0.5, 1 mg/kg (i.e. in the doses producing a pronounced antiarrhythmic effect) did not exert any influence on the arterial pressure and breathing.

To find out a negative inotropic effect on the heart tissue, two series of experiments have been carried out:

(1) the study of the effect of the preparation of this invention on the amplitude of the cardiac contractions of a frog's heart isolated according to Schtraube;

(2) the study of the preparation according to the present invention on the strength of cardiac contractions on narcotized (sodium ethaminal, 50–60 mg/kg intraperitoneally) rats and guinea pigs. The results of the first series of the experiments have shown that the preparation according to the present invention in a concentration of $10^{-6}$–$5.10^{-5}$ g/ml does not provide a negative inotropic effect. As regards the negative inotropic effect, quinidine is considerably superior to the preparation of the present invention. In a concentration of $10^{-4}$ to $3.10^{-4}$ g/ml quinidine causes, along with a sharp inhibition of the amplitude of cardiac contractions, arrhythmia. In the experiments of the second series it has been shown that the intravenous administration of the preparation according to the present invention in the doses of 0.1, 0.5, 1, 2 mg/kg, i.e. in the doses causing a 100% antiarrhythmic effect, provides no influence on the amplitude of cardiac contractions. Therefore, the preparation according to the present invention, in contrast to quinidine, possesses substantially no negative inotropic effect on the heart.

To investigate the character of the effect produced on the functions of the cardiac conductive system by the preparation according to the present invention, the ECG changes appearing in narcotized rats, cats, intact rabbits and dogs under the action of the preparation of this invention were studied. It has been found that the preparation, when administered intravenously in a dose of from 0.05 to 0.25 mg/kg, does not cause in rats any substantial effect on the ECG; in the dose of 0.5 mg/kg it causes deceleration of the atrioventricular conductivity and a certain rarification of the rhythm. Doses of 1–2 mg/kg increase the ranges PQ, QRS, QT, insignificantly R-R; the ripple S is deepened, the amplitude of the ripple T is uniformly increased. The intravenous administration of 4–6 mg/kg (sublethal and lethal doses) of the preparation according to the present invention results in a growing inhibition of conductivity along the cardiac conducting system. Quinidine and novocainamide in high doses also cause sharp disturbances of the rhythm of cardiac contractions. The ECG changes caused by the preparation according to the present invention show that the preparation lowers conductivity of the myocardium and, to a lesser extent, automatism of the sinus node. The effect of the preparation is retained for a long time. Sodium hydrocarbonate diminishes the inhibiting effect of the preparation on conductivity.

The effect of the pharmaceutical composition according to the present invention on the coronary blood circulation was studied in acute experiments on cats by the method of recording of the volume rate of the coronary blood flow. The intravenous administration of the preparation in the dose of 0.1 mg/kg does not provide any effect, but in the dose of 0.5 mg/kg in 40% of the animals it increases the coronary blood flow by 15–30%. The introduction of 1 mg/kg of the preparation results in an increased volume rate of the coronary blood flow by 30–80% during a long time. Therefore, the preparation according to the present invention, along with a pronounced antiarrhythmic effect, has a moderate coronarodilating effect as well.

The study of the effect produced by the preparation of the present invention on ion currents through the somatic membrane of neurons has shown that it selectively interacts with calcium and potassium channels of the membrane of neurons of mollusca, whereby the currents along these channels are suppressed.

The local anesthetic effect of the preparation was studied on 14 intact rabbits. It has been shown that it has a pronounced anesthetic effect and matches tetracaine hydrochloride in its anesthetic activity, though it is superior to the latter by more than 6 times in respect of the effect duration. As to the depth of anesthesia, the preparation of the present invention is inferior to tetracaine hydrochloride. The results of the experiments on determination of the ability of the preparation to cause infiltration anesthesia have shown that 10-15 minutes after intracutaneous administration, to rabbits, of 0.01-0.05% and 0.1% solutions of the preparation anesthesia occurs which is characterized by an increased threshold of a pain irritation; the duration of the effect is 20 to 48 hours. Under the same conditions of the experiment, the local anesthetic effect of a 0.5% solution of novocaine lasts for 90 minutes on the average. Therefore, the pharmaceutical composition according to the present invention possesses a pronounced and lasting local anesthetic effect.

The preparation according to the present invention has a weak central sedative effect, it does not provide any substantial effect on central adreno- and cholinergic processes and exerts but a weak serotonin-negative effect.

In doses of 1-5 mg/kg the preparation according to the present invention has a pronounced antiinflammatory effect.

The resorptive effect and toxicity of the preparation according to the present invention were studied on mice, rats, rabbits and dogs. Upon administration of the preparation in doses of 0.1-1 mg/kg intravenously, 1-5 mg/kg intraperitoneally, 5-20 mg/kg per os to different kinds of animals, no considerable changes in the general state of the animals are observed. In higher doses in mice and rats 5 minutes on the average after the administration of the preparation there occurs adynamia, delayed responses, weakening of the muscular tension, rarification and deepening of breathing, lowering of the body temperature. In sublethal and lethal doses the preparation causes more pronounced and intensive signs of the above-mentioned phenomena complemented by hypersalivation, diarrhea, acute disturbances of breathing.

In doses of 5-6 mg/kg intravenously the preparation according to the present invention causes death of dogs and in doses of 3-4 mg/kg it is lethal for rabbits.

In doses of 0.5-1 mg/kg the preparation provides no effect on diuresis of rats; protein and blood (sulphanylic acid test and benzidine test) are not detected in urina.

Experiments carried out on 12 guinea pigs and 6 rabbits demonstrate that the preparation according to the present invention possesses no allergenic effect.

In the dose of 1 mg/kg upon a single and lasting administration the pharmaceutical composition according to the present invention does not result in substantial changes as regards the content of sugar, protein and enzymes (transaminase, lactatedehydrogenase) in rats' blood.

On the basis of a comparative histological analysis of inner organs of laboratory animals (dogs, rabbits, rats) administered with different doses of the preparation according to the present invention during 6 months it can be stated that administration of the preparation to dogs per os in the doses of 1 and 5 mg/kg, to rabbits intravenously in the doses of 0.1 and 0.5 mg/kg and to rats per os in the dose of 1 mg/kg causes no destructive changes on the part of inner organs and tissues. A long-time administration of the preparation of this invention in the dose of 10 mg/kg causes structural changes in the inner organs.

In experiments with 317 pregnant rats which gave 2,377 feti it was shown that the preparation of the present invention was not a potentially teratogenic substance.

On the basis of the conducted macro- and microscopic investigations of the inner organs of the control and test animals it has been found that administration of the preparation subcutaneously and per os in doses of 0.5-2 mg/kg during 6 months does not cause, as it has been proven by observation over the animals for 2 years, the formation of neoplasms, as well as cellular and tissue atypism and anaplasia. Consequently, the preparation according to the present invention possesses no carcinogenic properties.

In acute experiments on dogs with recording to the arterial pressure, breathing and bioelectrical activity of the heart the effect of sodium bicarbonate has been studied at a cardiotoxic effect of the preparation according to the present invention.

It has been found that a drop-wise intravenous infusion of sodium bicarbonate in the form of a 4% solution in an amount of 100 to 200 ml equalizes distinctly pronounced electrocardiographic changes caused by the administration of toxic doses of the preparation according to the present invention within the period of 15 to 30 minutes after the beginning of the infusion. The reduction of the arterial pressure observed in overdosing of the preparation is levelled upon infusion of the solution of sodium bicarbonate in parallel with normalization of the ECG characteristics. A combined use of sodium bicarbonate and adrenalin ensured a more rapid levelling of hemodynamics and ECG changes in the animals.

The clinical study of the preparation according to the present invention was carried out on 200 patients suffering from various diseases accompanied by different cardiac rhythm disturbances (ischemic heart disease, diverse kinds of cardiomyopathy). The preparation was administered intravenously using 1-2 ampoules (0.5% solution of the preparation, 2 ml) and per os in tablets of 50 mg each (2-3 tablets a day during the first 2 days and 1-2 tablets a day during all following days). ECG characteristics, arterial pressure, heart beat rate and various parameters of hemodynamics were recorded.

The studies were conducted for both acute cases and a course treatment. It has been found that the preparation has a pronounced antiarrhythmic effect on patients with a stable form of ventricular and supraventricular extrasystole. Side effects (hypotension, changed heart beat rate, pulse, breathing) were not observed. The preparation is more efficient for course treatment in tabletted forms.

The pharmaceutical composition is useful in various preparative forms, preferably in the form of injection solutions and tablets.

Manufacture of the preparative forms is effected by conventional methods.

The active principle of the pharmaceutical composition according to the present invention—an alkaloid—lappaconitine hydrobromide is prepared following a known procedure in the following manner.

The aerial portion and roots (tubers) of the plant *Acontium leucostomum* are disintegrated. The disintegrated air-dry raw material is wetted with a 3% solution of sodium carbonate and 1 hour thereafter is poured with chloroform. 12 hours afterwards the chloroform is drained and the plant is treated with a fresh portion of chloroform. There are thus obtained 8 extracts which are combined and evaporated under vacuum to a small volume. From the concentrated chloroform extract the alkaloids are recovered by means of a 2% sulphuric acid. The combined acid extracts are washed with chloroform, alkalinized by soda and extracted with chloroform. The chloroform extract is evaporated and the residue is treated with acetone to give a commercial product—lappaconitine which is recrystallized from methanol. Methanolic solution of lappaconitine and hydrobromic acid are mixed. The precipitated lappaconitine hydrobromide is recrystallized from methanol to give white or white-yellowish bitter-taste crystals soluble in water, alcohol, better in methanol. M.p. is 216°–220° C., $[\alpha]_D^{24} = +27$ (alcohol); $C_{32}H_{44}O_8N_2 \cdot HBr$, molecular weight=664.9.

The preparation of this invention is administered per os intramuscularly or intravenously. The preparation is prescribed as tablet of 0.05 g 2–3 times a day or as injections of a 0.5% solution by portions of 2 ml 2–3 times a day. It is advisable that the preparation be administered per os before taking meals. The treatment course duration is 10 days. Side effects: in some cases weakness or giddeness passing after 10–15 minutes may be observed.

No contraindications against administration of the preparation have been revealed.

What is claimed is:

1. A method for the treatment of heart rhythm disturbances of both ventricular and supraventricular origin accompanying ischemic heart disease, myocardial infarctions and cardiomyopathy, which comprises administering to a subject in need of such treatment, a pharmaceutical composition containing in single dose form, from about 0.03 to about 1 mg/kg of body weight of lappaconitine hydrobromide and a pharmaceutically acceptable carrier.

2. The method of claim 1 wherein the lappaconitine hydrobromide is administered per os.

3. The method of claim 1 wherein the lappaconitine hydrobromide is administered by injection.

4. The method of claim 1 wherein from about 0.05 to 1 mg/kg of lappaconitine hydrobromide is administered to the subject.

* * * * *